United States Patent
Girdhar et al.

(10) Patent No.: US 11,058,444 B2
(45) Date of Patent: Jul. 13, 2021

(54) ELECTRICALLY ENHANCED RETRIEVAL OF MATERIAL FROM VESSEL LUMENS

(71) Applicant: Covidien LP, Mansfield, MA (US)

(72) Inventors: Gaurav Girdhar, Ladera Ranch, CA (US); Hoai Nguyen, Santa Ana, CA (US); Andy Huynh, Westminster, CA (US); Ashok Nageswaran, Irvine, CA (US); Christopher Andrews, Lake Elsinore, CA (US)

(73) Assignee: COVIDIEN LP, Mansfield, MA (US)

( * ) Notice: Subject to any disclaimer, the term of this patent is extended or adjusted under 35 U.S.C. 154(b) by 404 days.

(21) Appl. No.: 15/838,214

(22) Filed: Dec. 11, 2017

(65) Prior Publication Data
US 2019/0175199 A1    Jun. 13, 2019

(51) Int. Cl.
*A61B 17/22*    (2006.01)
*A61F 2/95*    (2013.01)
(Continued)

(52) U.S. Cl.
CPC ...... *A61B 17/22031* (2013.01); *A61B 17/221* (2013.01); *A61B 18/00* (2013.01);
(Continued)

(58) Field of Classification Search
CPC . A61B 17/22031; A61B 17/221; A61B 18/00; A61B 2017/00017;
(Continued)

(56) References Cited

U.S. PATENT DOCUMENTS

| 5,549,626 A | 8/1996 | Miller et al. |
| 5,972,019 A | 10/1999 | Engelson et al. |

(Continued)

FOREIGN PATENT DOCUMENTS

| EP | 2319575 B1 | 11/2013 |
| EP | 2490764 B1 | 9/2014 |

(Continued)

OTHER PUBLICATIONS

U.S. Appl. No. 15/838,230, filed Dec. 11, 2017.
(Continued)

*Primary Examiner* — George J Ulsh
*Assistant Examiner* — Andrew P. Restaino
(74) *Attorney, Agent, or Firm* — Fortem IP LLP; Matthew Lincicum

(57) ABSTRACT

Retrieval of material from vessel lumens can be improved by electrically enhancing attachment of the material to the removal device. The removal device can have a core assembly that includes a hypotube coupled to a first electrical terminal and a pushwire coupled to a second electrical terminal, the pushwire extending through the hypotube lumen. An insulating layer separates the hypotube and the pushwire, and an interventional element is coupled to a distal end of the pushwire. The interventional element can be disposed adjacent to a thrombus. An electrical signal is delivered to the interventional element to promote adhesion of the thrombus to the interventional element. The electrical signal can optionally be a periodic waveform, and the total energy delivered can be between 0.75-24,000 mJ and the peak current delivered via the electrical signal can be between 0.5-5 mA.

28 Claims, 7 Drawing Sheets

(51) Int. Cl.
*A61B 18/00* (2006.01)
*A61B 17/221* (2006.01)
A61B 90/00 (2016.01)
A61B 17/00 (2006.01)
A61F 2/966 (2013.01)

(52) U.S. Cl.
CPC ...... *A61F 2/95* (2013.01); *A61B 2017/00017* (2013.01); *A61B 2017/00154* (2013.01); *A61B 2017/00867* (2013.01); *A61B 2017/00929* (2013.01); *A61B 2017/2215* (2013.01); *A61B 2017/22034* (2013.01); *A61B 2017/22042* (2013.01); *A61B 2090/3966* (2016.02); *A61F 2/966* (2013.01); *A61F 2002/9511* (2013.01); *A61F 2002/9528* (2013.01)

(58) Field of Classification Search
CPC ........... A61B 2017/00154; A61B 2017/00867; A61B 2017/00929; A61B 2017/22034; A61B 2017/22042; A61B 2017/2215; A61B 2090/3966; A61F 2002/9511; A61F 2002/9528; A61F 2/95; A61F 2/966; A61N 1/04; A61N 1/05
USPC ....................................................... 606/127
See application file for complete search history.

(56) References Cited

U.S. PATENT DOCUMENTS

| | | | |
|---|---|---|---|
| 6,022,336 A | 2/2000 | Zadno-Azizi et al. | |
| 6,059,779 A | 5/2000 | Mills | |
| 6,315,794 B1 | 11/2001 | Richter | |
| 6,540,733 B2 | 4/2003 | Constantz et al. | |
| 6,663,650 B2 | 12/2003 | Sepetka et al. | |
| 7,556,624 B2 | 7/2009 | Laufer et al. | |
| 8,038,674 B2 | 10/2011 | Schmaltz et al. | |
| 8,382,821 B2 | 2/2013 | Richter | |
| 8,603,014 B2 | 12/2013 | Alleman et al. | |
| 8,837,800 B1 | 9/2014 | Bammer et al. | |
| 8,888,788 B2 | 11/2014 | Adams et al. | |
| 9,011,431 B2 | 4/2015 | Long et al. | |
| 9,039,753 B2 | 5/2015 | Thramann | |
| 9,119,656 B2 | 9/2015 | Bose et al. | |
| 9,126,018 B1 | 9/2015 | Garrison | |
| 9,179,971 B2 | 11/2015 | Kirschenman | |
| 9,211,132 B2 | 12/2015 | Bowman | |
| 9,241,699 B1 | 1/2016 | Kume et al. | |
| 9,265,512 B2 | 2/2016 | Garrison et al. | |
| 9,308,007 B2 | 4/2016 | Cully et al. | |
| 9,399,118 B2 | 7/2016 | Kume et al. | |
| 9,445,828 B2 | 9/2016 | Turjman et al. | |
| 9,445,829 B2 | 9/2016 | Brady et al. | |
| 9,492,637 B2 | 11/2016 | Garrison et al. | |
| 9,539,022 B2 | 1/2017 | Bowman | |
| 9,561,345 B2 | 2/2017 | Garrison et al. | |
| 9,579,119 B2 | 2/2017 | Cully et al. | |
| 9,585,741 B2 | 3/2017 | Ma | |
| 9,642,635 B2 | 5/2017 | Vale et al. | |
| 9,655,633 B2 | 5/2017 | Leynov et al. | |
| 9,681,882 B2 | 6/2017 | Wilson et al. | |
| 9,713,730 B2 | 7/2017 | Mathur et al. | |
| 9,737,318 B2 | 8/2017 | Monstadt et al. | |
| 9,770,251 B2 | 9/2017 | Bowman et al. | |
| 9,795,400 B2 | 10/2017 | Davidson | |
| 9,801,643 B2 | 10/2017 | Hansen et al. | |
| 9,861,783 B2 | 1/2018 | Garrison et al. | |
| 9,993,257 B2 | 6/2018 | Losordo et al. | |
| 10,028,782 B2 | 7/2018 | Orion | |
| 10,029,008 B2 | 7/2018 | Creighton | |
| 10,039,906 B2 | 8/2018 | Kume et al. | |
| 2001/0001314 A1 | 5/2001 | Davison et al. | |
| 2002/0013311 A1 | 1/2002 | Hellberg et al. | |
| 2002/0133111 A1 | 9/2002 | Shadduck et al. | |
| 2004/0219660 A1 | 11/2004 | Dev et al. | |
| 2006/0045861 A1 | 3/2006 | Bejger et al. | |
| 2006/0089638 A1 | 4/2006 | Carmel et al. | |
| 2006/0262489 A1 | 11/2006 | Vaisman et al. | |
| 2008/0045881 A1 | 2/2008 | Teitelbaum et al. | |
| 2008/0262489 A1 | 10/2008 | Steinke et al. | |
| 2008/0294181 A1* | 11/2008 | Wensel ................ A61B 17/221 606/159 |
| 2009/0054918 A1 | 2/2009 | Henson | |
| 2011/0196478 A1 | 8/2011 | Torosoff | |
| 2011/0301549 A1 | 12/2011 | Hartmann | |
| 2011/0301594 A1* | 12/2011 | Orion ................ A61B 18/1492 606/41 |
| 2013/0030461 A1 | 1/2013 | Marks et al. | |
| 2013/0072960 A1 | 3/2013 | Schneider et al. | |
| 2013/0281788 A1 | 10/2013 | Garrison | |
| 2014/0025152 A1* | 1/2014 | Headley ................ A61F 2/962 623/1.11 |
| 2014/0276074 A1 | 9/2014 | Warner | |
| 2014/0277013 A1 | 9/2014 | Sepetka et al. | |
| 2014/0309673 A1 | 10/2014 | Dacuycuy et al. | |
| 2014/0343595 A1 | 11/2014 | Monstadt et al. | |
| 2014/0364896 A1 | 12/2014 | Consigny | |
| 2015/0359547 A1 | 12/2015 | Vale et al. | |
| 2016/0015402 A1 | 1/2016 | Brady et al. | |
| 2016/0015935 A1 | 1/2016 | Chan et al. | |
| 2016/0106448 A1 | 4/2016 | Brady et al. | |
| 2016/0106449 A1 | 4/2016 | Brady et al. | |
| 2016/0113663 A1 | 4/2016 | Brady et al. | |
| 2016/0113665 A1 | 4/2016 | Brady et al. | |
| 2016/0151618 A1 | 6/2016 | Powers et al. | |
| 2016/0157985 A1 | 6/2016 | Vo et al. | |
| 2016/0199620 A1 | 7/2016 | Pokorney et al. | |
| 2016/0228681 A1 | 8/2016 | Di Palma et al. | |
| 2016/0296690 A1 | 10/2016 | Kume et al. | |
| 2016/0302808 A1 | 10/2016 | Loganathan et al. | |
| 2016/0331377 A1 | 11/2016 | Divino et al. | |
| 2016/0375180 A1 | 12/2016 | Anzai | |
| 2017/0079766 A1 | 3/2017 | Wang et al. | |
| 2017/0079767 A1 | 3/2017 | Leon-Yip | |
| 2017/0086862 A1 | 3/2017 | Vale et al. | |
| 2017/0100143 A1 | 4/2017 | Grandfield | |
| 2017/0105743 A1 | 4/2017 | Vale et al. | |
| 2017/0164963 A1 | 6/2017 | Goyal | |
| 2017/0215902 A1 | 8/2017 | Leynov et al. | |
| 2017/0215955 A1* | 8/2017 | Hancock ............ A61B 18/1815 |
| 2017/0224953 A1 | 8/2017 | Tran et al. | |
| 2017/0281909 A1 | 10/2017 | Northrop et al. | |
| 2017/0290599 A1 | 10/2017 | Youn et al. | |
| 2017/0367707 A1 | 12/2017 | Divino | |
| 2018/0049762 A1 | 2/2018 | Seip et al. | |
| 2018/0084982 A1 | 3/2018 | Yamashita et al. | |
| 2018/0116717 A1 | 5/2018 | Taff et al. | |
| 2018/0132876 A1 | 5/2018 | Zaidat | |
| 2018/0133436 A1 | 5/2018 | Garrison et al. | |
| 2018/0140314 A1 | 5/2018 | Goyal et al. | |
| 2018/0140315 A1 | 5/2018 | Bowman et al. | |
| 2018/0140354 A1 | 5/2018 | Lam et al. | |
| 2018/0161541 A1 | 6/2018 | Haldis et al. | |
| 2018/0185614 A1 | 7/2018 | Garrison et al. | |
| 2018/0236221 A1 | 8/2018 | Opie et al. | |
| 2018/0303595 A1 | 10/2018 | Opie et al. | |
| 2019/0038438 A1 | 2/2019 | John et al. | |
| 2019/0046119 A1 | 2/2019 | Oxley | |
| 2019/0175200 A1 | 6/2019 | Girdhar et al. | |
| 2019/0262069 A1 | 8/2019 | Taff et al. | |
| 2019/0388097 A1 | 12/2019 | Girdhar et al. | |
| 2019/0388107 A1 | 12/2019 | Girdhar et al. | |
| 2019/0388111 A1 | 12/2019 | Nguyen et al. | |
| 2019/0388112 A1 | 12/2019 | Nguyen et al. | |
| 2020/0297367 A1 | 9/2020 | Girdhar et al. | |
| 2020/0297410 A1 | 9/2020 | Nguyen et al. | |

FOREIGN PATENT DOCUMENTS

| | | |
|---|---|---|
| EP | 3184067 A1 | 6/2017 |
| JP | 10290805 A | 11/1998 |
| JP | 2014004219 A | 1/2014 |
| JP | 2018118132 A | 8/2018 |

(56) References Cited

FOREIGN PATENT DOCUMENTS

| | | | |
|---|---|---|---|
| KR | 20180102877 | A | 9/2018 |
| WO | 2010061376 | A1 | 6/2010 |
| WO | 2014079148 | A1 | 5/2014 |
| WO | 2015141317 | A1 | 9/2015 |
| WO | 2016198947 | A1 | 12/2016 |
| WO | 2017192999 | A1 | 11/2017 |
| WO | 2018019829 | A1 | 2/2018 |
| WO | 2018033401 | A1 | 2/2018 |
| WO | 2018046408 | A2 | 3/2018 |
| WO | 2018127796 | A1 | 7/2018 |
| WO | 2018137029 | A1 | 8/2018 |
| WO | 2018137030 | A1 | 8/2018 |
| WO | 2018145212 | A1 | 8/2018 |
| WO | 2018156813 | A1 | 8/2018 |
| WO | 2018172891 | A1 | 9/2018 |
| WO | 2018187776 | A1 | 10/2018 |
| WO | 2019102307 | A1 | 5/2019 |
| WO | 2019246377 | A2 | 12/2019 |

OTHER PUBLICATIONS

Fort, Stephen, et al., "'Fused-Gold' vs. 'Bare' stainless steel NIRflex stents of the same geometric design in diseased native coronary arteries. Long-term results from the NIR TOP Study", Euro Interv 2007; 3:256-261.

International Search Report and Written Opinion dated May 25, 2020, International Application No. PCT/US20/22463, 10 pages.

\* cited by examiner

ELECTRICALLY ENHANCED RETRIEVAL OF MATERIAL FROM VESSEL LUMENS

TECHNICAL FIELD

The present technology relates generally to devices and methods for removing obstructions from body lumens. Some embodiments of the present technology relate to devices and methods for electrically enhanced removal of clot material from blood vessels.

BACKGROUND

Many medical procedures use medical device(s) to remove an obstruction (such as clot material) from a body lumen, vessel, or other organ. An inherent risk in such procedures is that mobilizing or otherwise disturbing the obstruction can potentially create further harm if the obstruction or a fragment thereof dislodges from the retrieval device. If all or a portion of the obstruction breaks free from the device and flows downstream, it is highly likely that the free material will become trapped in smaller and more tortuous anatomy. In many cases, the physician will no longer be able to use the same retrieval device to again remove the obstruction because the device may be too large and/or immobile to move the device to the site of the new obstruction.

Procedures for treating ischemic stroke by restoring flow within the cerebral vasculature are subject to the above concerns. The brain relies on its arteries and veins to supply oxygenated blood from the heart and lungs and to remove carbon dioxide and cellular waste from brain tissue. Blockages that interfere with this blood supply eventually cause the brain tissue to stop functioning. If the disruption in blood occurs for a sufficient amount of time, the continued lack of nutrients and oxygen causes irreversible cell death. Accordingly, it is desirable to provide immediate medical treatment of an ischemic stroke.

To access the cerebral vasculature, a physician typically advances a catheter from a remote part of the body (typically a leg) through the abdominal vasculature and into the cerebral region of the vasculature. Once within the cerebral vasculature, the physician deploys a device for retrieval of the obstruction causing the blockage. Concerns about dislodged obstructions or the migration of dislodged fragments increases the duration of the procedure at a time when restoration of blood flow is paramount. Furthermore, a physician might be unaware of one or more fragments that dislodge from the initial obstruction and cause blockage of smaller more distal vessels.

Many physicians currently perform thrombectomies (i.e. clot removal) with stents to resolve ischemic stroke. Typically, the physician deploys a stent into the clot in an attempt to push the clot to the side of the vessel and re-establish blood flow. Tissue plasminogen activator ("tPA") is often injected into the bloodstream through an intravenous line to break down a clot. However, it takes time for the tPA to reach the clot because the tPA must travel through the vasculature and only begins to break up the clot once it reaches the clot material. tPA is also often administered to supplement the effectiveness of the stent. Yet, if attempts at clot dissolution are ineffective or incomplete, the physician can attempt to remove the stent while it is expanded against or enmeshed within the clot. In doing so, the physician must effectively drag the clot through the vasculature, in a proximal direction, into a guide catheter located within vessels in the patient's neck (typically the carotid artery). While this procedure has been shown to be effective in the clinic and easy for the physician to perform, there remain some distinct disadvantages using this approach.

For example, one disadvantage is that the stent may not sufficiently retain the clot as it pulls the clot to the catheter. In such a case, some or all of the clot might remain the vasculature. Another risk is that, as the stent mobilizes the clot from the original blockage site, the clot might not adhere to the stent as the stent is withdrawn toward the catheter. This is a particular risk when passing through bifurcations and tortuous anatomy. Furthermore, blood flow can carry the clot (or fragments of the clot) into a branching vessel at a bifurcation. If the clot is successfully brought to the end of the guide catheter in the carotid artery, yet another risk is that the clot may be "stripped" or "sheared" from the stent as the stent enters the guide catheter.

In view of the above, there remains a need for improved devices and methods that can remove occlusions from body lumens and/or vessels.

SUMMARY

Mechanical thrombectomy (i.e., clot-grabbing and removal) has been effectively used for treatment of ischemic stroke. Although most clots can be retrieved in a single pass attempt, there are instances in which multiple attempts are needed to fully retrieve the clot and restore blood flow through the vessel. Additionally, there exist complications due to detachment of the clot from the interventional element during the retrieval process as the interventional element and clot traverse through tortuous intracranial arterial vascular anatomy. For example, the detached clot or clot fragments can obstruct other arteries leading to secondary strokes. The failure modes that contribute to clot release during retrieval are: (a) boundary conditions at bifurcations; (b) changes in vessel diameter; and (c) vessel tortuosity, amongst others.

Certain blood components, such as platelets and coagulation proteins, display negative electrical charges. If the interventional element can be made to exhibit positive charges (for example by application of direct current), there can be potential improvement in clot capture and retention and a reduced number of device passages or attempts to fully retrieve the clot. Embodiments of the present technology provide an interventional element with a positive electrical charge so as to attract negatively charged blood components, thereby improving attachment of the thrombus to the interventional element. The delivery electrode and return electrode can be integrated together into a multi-component or multi-channel core assembly coupled to the interventional element. A central conductive shaft or pushwire is coupled to the interventional element at its distal end, and a conductive tubular member or hypotube surrounds the pushwire along at least a portion of its length. The central pushwire can be coupled to a positive electrical terminal and the surrounding hypotube can be coupled to a negative electrical terminal. An electrically insulating layer can separate the central pushwire and the surrounding hypotube. An additional electrically insulating layer can surround the hypotube along a proximal portion, leaving a distalmost portion of the hypotube exposed so that the return circuit can be completed in the presence of blood or other electrolytic media. When voltage is applied at the terminals and the interventional element placed in the presence of blood (or any other electrolytic medium), current flows from the interventional element, through the blood, and to the distal portion of the hypotube which serves as the return electrode.

While applying a direct current (DC) electrical signal to negatively charge the thrombectomy device can improve attachment of the thrombus to the retrieval device, the inventors have discovered particularly effective waveforms and power delivery parameters for promoting thrombus attachment. It is important to provide sufficient current and power to enhance clot-adhesion without ablating tissue or generating new clots (i.e., the delivered power should not be significantly thrombogenic). The clot-adhesion effect appears to be driven by the peak current of the delivered electrical signal. Periodic (e.g., pulse-width modulated or pulsed direct current) waveforms can advantageously provide the desired peak current without delivering excessive total energy. In particular, non-square periodic waveforms can be especially effective in providing the desired peak current without delivering excessive total energy or electrical charge to the interventional element. In some embodiments, the overall charge delivered can be between about 30-1200 mC, the total energy delivered can be between about 120-24,000 mJ, and/or the peak current delivered can be between about 0.5-5 mA. In at least some embodiments, the total energy delivery time can be no more than 2 minutes.

The present technology is illustrated, for example, according to various aspects described below. Various examples of aspects of the present technology are described as numbered clauses (1, 2, 3, etc.) for convenience. These are provided as examples and do not limit the present technology. It is noted that any of the dependent clauses may be combined in any combination, and placed into a respective independent clause, e.g., clause (1, 14, 27, etc.). The other clauses can be presented in a similar manner.

1. A medical device comprising:
   a core assembly having a distal portion configured to be intravascularly positioned at a treatment site within a blood vessel lumen, the core assembly comprising:
      a hypotube coupled to a first electrical terminal, the hypotube having a proximal portion, a distal portion, and a lumen extending therethrough;
      a pushwire coupled to a second electrical terminal, the pushwire extending through the hypotube lumen; and
      an insulating layer disposed between the hypotube and the pushwire, the insulating layer extending from the proximal portion of the hypotube to the distal portion of the hypotube; and
   an interventional element coupled to a distal end of the pushwire.

2. The medical device of Clause 1, wherein the interventional element comprises a thrombectomy device.

3. The medical device of Clause 1, wherein the interventional element comprises a stent retriever.

4. The medical device of Clause 1, wherein the interventional element comprises a removal device.

5. The medical device of Clause 1, wherein the interventional element comprises a catheter.

6. The medical device of any one of Clauses 1-5, wherein the interventional element is in electrical communication with the pushwire.

7. The medical device of any one of Clauses 1-6, wherein the first electrical terminal is negative and the second electrical terminal is positive.

8. The medical device of any one of Clauses 1-7, further comprising a second insulating layer disposed around an outer surface of a proximal portion of the hypotube.

9. The medical device of Clause 8, wherein the outer surface of a distal portion of the hypotube is uncovered by the second insulating layer.

10. The medical device of any one of Clauses 1-9, wherein the insulating layer comprises PTFE, polyimide, EETFE, or a dielectric polymer.

11. The medical device of any one of Clauses 1-10, wherein the pushwire is fixed with respect to the hypotube.

12. The medical device of any one of Clauses 1-11, further comprising a radiopaque marker disposed at a distal end of the pushwire.

13. The medical device of any one of Clauses 1-12, wherein, when the interventional element is in the presence of an electrolytic medium and voltage is supplied to the first and second electrical terminals, current flows from the interventional element to the hypotube.

14. The medical device of any one of Clauses 1-13, wherein a portion of the interventional element is coated with a non-conductive material.

15. A medical device delivery system, comprising:
   a medical device coupled to a distal end of an elongate shaft, the shaft configured to be electrically coupled to a first terminal;
   an elongate tubular member surrounding at least a portion of the shaft, the tubular member configured to be electrically coupled to a second terminal;
   a first insulating material separating the shaft and the tubular member; and
   a second insulating material surrounding at least a portion of the tubular member.

16. The medical device delivery system of Clause 15, wherein the positions of the shaft and the tubular member are fixed relative to one another.

17. The medical device delivery system of any one of Clauses 15-16, wherein the tubular member is not slidable with respect to the shaft.

18. The medical device delivery system of any one of Clauses 15-17, wherein the medical device comprises a thrombectomy device.

19. The medical device delivery system of any one of Clauses 15-17, wherein the medical device comprises a stent retriever.

20. The medical device delivery system of any one of Clauses 15-17, wherein the medical device comprises a removal device.

21. The medical device delivery system of any one of Clauses 15-20, wherein the medical device is in electrical communication with the shaft.

22. The medical device delivery system of any one of Clauses 15-21, wherein the first electrical terminal is positive and the second electrical terminal is negative.

23. The medical device delivery system of any one of Clauses 15-22, wherein an outer surface of a distal portion of the tubular member is uncovered by the second insulating material.

24. The medical device delivery system of any one of Clauses 15-23, wherein the first insulating material and the second insulating material each comprises PTFE, polyimide, ETFE, or a dielectric polymer.

25. The medical device delivery system of any one of Clauses 15-24, further comprising a radiopaque marker disposed at a distal end of the shaft.

26. The medical device delivery system of any one of Clauses 15-25, wherein, when the medical device is in the presence of an electrolytic medium and voltage is supplied to the first and second electrical terminals, current flows from the medical device to the tubular member.

27. The medical device delivery system of any one of Clauses 15-26, wherein a portion of the medical device is coated with a non-conductive material.

28. A method, comprising:
advancing a core assembly through a catheter to a target site in the body, the core assembly comprising:
a hypotube coupled to a first electrical terminal;
a pushwire coupled to a second electrical terminal, the pushwire extending through a lumen of the hypotube; and
an interventional element coupled to a distal end of the pushwire;
supplying electrical current to the second electrical terminal.

29. The method of Clause 28, further comprising ceasing the supplying of electrical current to the second electrical terminal after a first time period.

30. The method of Clause 29, further comprising, after ceasing the supplying of electrical current, proximally retracting the core assembly with respect to the catheter.

31. The method of any one of Clauses 29-30, wherein the first time period is less than about 5 minutes.

32. The method of any one of Clauses 29-31, wherein the first time period is less than about 2 minutes.

33. The method of any one of Clauses 28-32, wherein the target site in the body is proximate to or adjacent to a thrombus in a blood vessel.

34. The method of any one of Clauses 28-33, further comprising, after advancing the core assembly through the catheter, expanding the interventional element adjacent to a thrombus in a blood vessel.

35. The method of any one of Clauses 28-34, wherein the interventional element comprises a thrombectomy device.

36. The method of any one of Clauses 28-34, wherein the interventional element comprises a stent retriever.

37. The method of any one of Clauses 28-34, wherein the interventional element comprises a removal device.

38. The method of any one of Clauses 28-37, wherein the interventional element is in electrical communication with the pushwire.

39. The method of any one of Clauses 28-38, further comprising a second insulating layer disposed around an outer surface of a proximal portion of the hypotube.

40. The method of any one of Clauses 28-39, wherein the outer surface of a distal portion of the hypotube is uncovered by the second insulating layer.

41. The method of any one of Clauses 28-40, wherein the pushwire is fixed with respect to the hypotube.

42. A method for thrombectomy, comprising:
disposing an interventional element adjacent to a thrombus within a blood vessel;
promoting adhesion of the thrombus to the interventional element by delivering an electrical signal to the interventional element (the electrical signal optionally comprising a periodic waveform or a constant direct current),
wherein the total energy delivered via the electrical signal is between 0.75-24,000 mJ, or 120-24,000 mJ, and
wherein the peak current delivered via the electrical signal is between 0.5-5 mA.

43. The method of Clause 42, wherein the electrical signal is delivered for no more than 2 minutes.

44. The method of any one of Clauses 42-43, wherein the total energy delivered via the electrical signal is between 120-5000 mJ.

45. The method of any one of Clauses 42-44, wherein the total charge delivered via the electrical signal is between 30-1200 mC.

46. The method of any one of Clauses 42-45, wherein the total charge delivered via the electrical signal is between 120-160 mC.

47. The method of any one of Clauses 42-46, wherein the frequency of the electrical signal is between 1 Hz and 1 MHz.

48. The method of Clause 47, wherein the frequency of the electrical signal is between 1 Hz and 1 kHz.

49. The method of any one of Clauses 42-48, wherein the duty cycle of the electrical signal is between 5-99%.

50. The method of Clause 49, wherein the duty cycle of the electrical signal is between 5-20%.

51. The method of any one of Clauses 42-46, wherein the waveform comprises a non-square waveform.

52. The method of any one of Clauses 42-47, wherein the waveform comprises a composite waveform including the superposition of a square waveform and a non-square waveform.

53. The method of Clause 52, wherein the non-square waveform comprises a triangular waveform.

54. The method of any one of Clauses 42-53, wherein the interventional element comprises an electrically conductive self-expandable device.

55. The method of any one of Clauses 42-54, further comprising removing the thrombus from the blood vessel.

56. The method of any one of Clauses 42-55, further comprising retracting the interventional element, thereby displacing the thrombus.

57. The method of any one of Clauses 42-56, wherein delivering the electrical signal to the interventional element is not substantially thrombogenic.

58. The method of any one of Clauses 42-57, wherein the interventional element comprises a stent retriever.

59. The method of any one of Clauses 42-57, wherein the interventional element comprises a thrombectomy device.

60. The method of any one of Clauses 42-57, wherein the interventional element comprises a removal device.

61. The method of any one of Clauses 42-57, wherein the interventional element comprises a catheter.

62. A method for thrombectomy, comprising:
positioning an interventional element proximate to a thrombus, the interventional element in electrical communication with a power source;
supplying an electrical waveform from the power source to the interventional element,
wherein the total charge supplied via the waveform is between 30-240 mC, and
wherein the waveform is supplied for no more than 2 minutes.

63. The method of Clause 62, wherein a total energy delivered via the waveform is between 120-24,000 mJ.

64. The method of Clause 63, wherein the total energy supplied via the waveform is between 120-5000 mJ.

65. The method of any one of Clauses 62-64, wherein a peak current delivered via the waveform is between 0.5-5 mA.

66. The method of any one of Clauses 62-65, wherein the total charge delivered via the waveform is between 30-1200 mC.

67. The method of Clause 66, wherein the total charge delivered via the waveform is between 120-160 mC.

68. The method of any one of Clauses 62-67, wherein the frequency of the electrical waveform is between 1 Hz to 1 MHz.

69. The method of Clause 68, wherein the frequency of the electrical waveform is between 1 Hz to 1 kHz 70. The method of any one of Clauses 62-69, wherein the duty cycle of the electrical waveform is between 5-99%.

71. The method of Clause 70, wherein the duty cycle of the electrical waveform is between 5-20%.

72. The method of any one of Clauses 62-71, wherein the waveform comprises a non-square waveform.

73. The method of any one of Clauses 62-72, wherein the waveform comprises a composite waveform including the superposition of a square waveform and a non-square waveform.

74. The method of Clause 73, wherein the non-square waveform comprises a triangular waveform.

75. The method of any one of Clauses 62-74, wherein the interventional element comprises an electrically conductive self-expandable device.

76. The method of any one of Clauses 62-75, further comprising removing the thrombus from a blood vessel.

77. The method of any one of Clauses 62-76, further comprising retracting the interventional element, thereby displacing the thrombus.

78. The method of any one of Clauses 62-77, wherein delivering the waveform to the interventional element is not substantially thrombogenic.

79. The method of any one of Clauses 62-78, wherein the interventional element comprises a stent retriever.

80. The method of any one of Clauses 62-78, wherein the interventional element comprises a thrombectomy device.

81. The method of any one of Clauses 62-78, wherein the interventional element comprises a removal device.

82. The method of any one of Clauses 62-78, wherein the interventional element comprises a catheter.

83. A system for removing a thrombus, the system comprising:
an interventional element configured to be disposed proximate to or adjacent to a thrombus within a blood vessel;
a current generator in electrical communication with the interventional element, the current generator configured to deliver an electrical signal to the interventional element for a predetermined time period (the electrical signal optionally comprising a periodic waveform or a constant direct current),
wherein the total energy delivered via the electrical signal over the predetermined time period is between 0.75-24,000 mJ, or 120-24,000 mJ, and
wherein the peak current delivered via the electrical signal is between 0.5-5 mA.

84. The system of Clause 83, wherein the current generator comprises a power source and a processor coupled to a memory, the memory storing the instructions for causing the power source to deliver the electrical signal to the interventional element.

85. The system of Clause 83, wherein the current generator comprises a power source and drive circuitry configured to deliver the electrical signal to the interventional element 86. The system of any one of Clauses 83-85, wherein the predetermined time period is no more than 5 minutes.

87. The system of Clause 86, wherein the predetermined time period is no more than 2 minutes.

88. The system of any one of Clauses 83-87, wherein the total energy delivered via the electrical signal over the predetermined time period is between 120-5000 mJ.

89. The system of any one of Clauses 83-88, wherein the total charge delivered via the electrical signal over the predetermined time period is between 30-1200 mC.

90. The system of Clause 89, wherein the total charge delivered via the electrical signal over the predetermined time period is between 120-160 mC.

91. The system of any one of Clauses 83-90, wherein the frequency of the electrical signal is between 1 Hz to 1 MHz.

92. The system of Clause 91, wherein the frequency of the electrical signal is between 1 Hz to 1 kHz 93. The system of any one of Clauses 83-92, wherein the duty cycle of the electrical signal is between 5-99%.

94. The system of Clause 93, wherein the duty cycle of the electrical signal is between 5-20%.

95. The system of any one of Clauses 83-94, wherein the waveform comprises a non-square waveform.

96. The system of any one of Clauses 83-96, wherein the waveform comprises a composite waveform including the superposition of a square waveform and a non-square waveform.

97. The system of Clause 96, wherein the non-square waveform comprises a triangular waveform.

98. The system of any one of Clauses 83-97, wherein the interventional element comprises an electrically conductive self-expandable device.

99. The system of any one of Clauses 83-97, wherein the interventional element comprises a stent retriever.

100. The system of any one of Clauses 83-97, wherein the interventional element comprises a thrombectomy device.

101. The system of any one of Clauses 83-97, wherein the interventional element comprises a removal device.

102. The system of any one of Clauses 83-97, wherein the interventional element comprises a catheter.

Additional features and advantages of the present technology are described below, and in part will be apparent from the description, or may be learned by practice of the present technology. The advantages of the present technology will be realized and attained by the structure particularly pointed out in the written description and claims hereof as well as the appended drawings.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

DETAILED DESCRIPTION

The present technology provides devices, systems, and methods for removing clot material from a blood vessel lumen. Although many of the embodiments are described below with respect to devices, systems, and methods for treating a cerebral or intracranial embolism, other applications and other embodiments in addition to those described herein are within the scope of the technology. For example, the retrieval devices of the present technology may be used to remove emboli from body lumens other than blood vessels (e.g., the digestive tract, etc.) and/or may be used to remove emboli from blood vessels outside of the brain (e.g., pulmonary blood vessels, blood vessels within the legs, etc.). In addition, the retrieval devices of the present technology may be used to remove luminal obstructions other than clot material (e.g., plaque, resected tissue, foreign material, etc.).

Select Embodiments of Electrically Enhanced Retrieval Devices

Figure 1A:
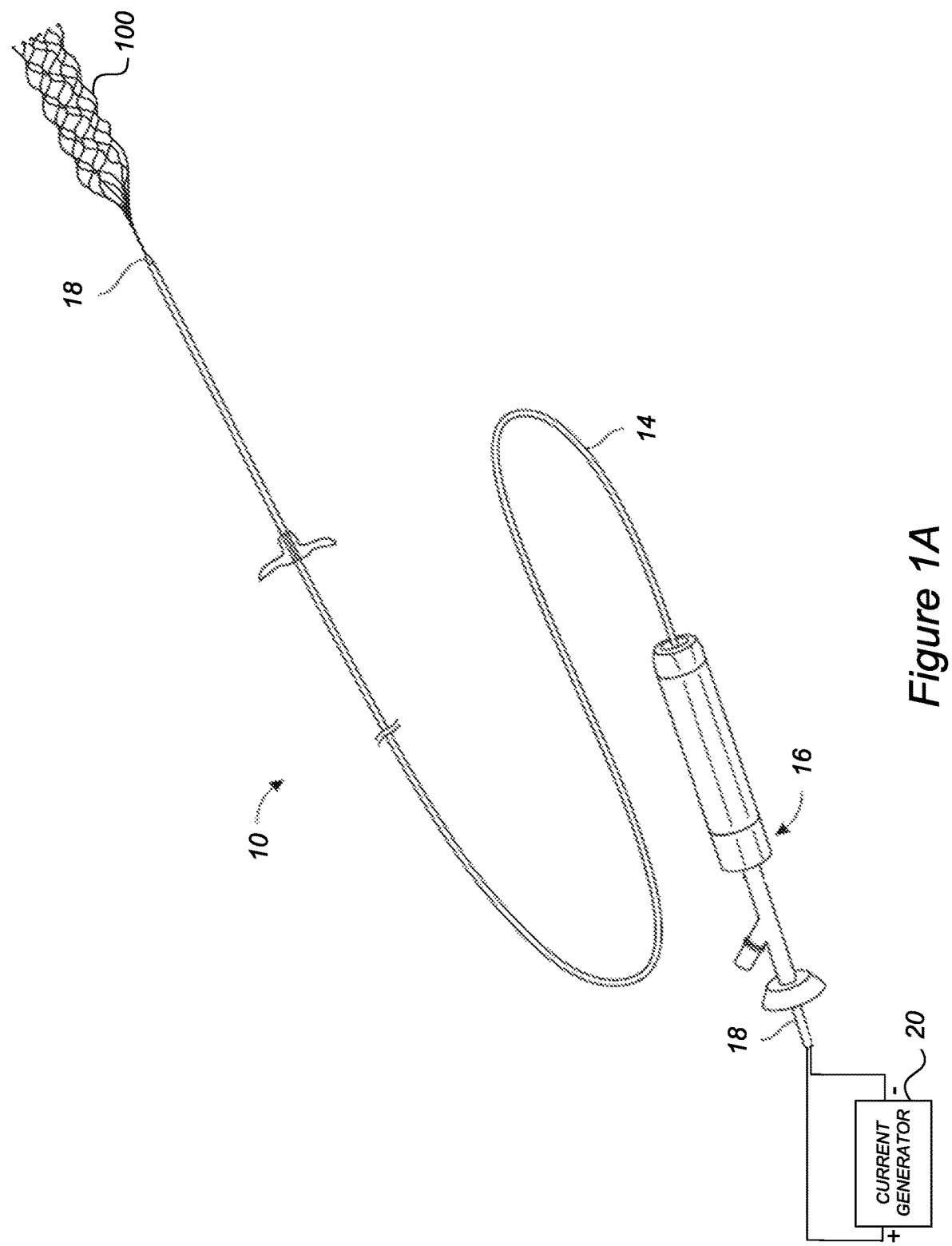
FIG. 1A shows a perspective view of a treatment system with an electrically enhanced retrieval device, in accordance with one or more embodiments of the present disclosure.

FIG. 1A illustrates a view of a treatment system 10 according to one or more embodiments of the present technology. According to some embodiments, for example, as shown in FIG. 1, the treatment system 10 can include an interventional element 100 coupled to a core assembly 18, and a delivery catheter 14 connected to a handle 16. The handle 16 shown provides proximal access to the core assembly 18 that engages the interventional element 100 at a distal end thereof. The delivery catheter 14 can be positioned coaxially over the core assembly 18. According to some embodiments, a current generator 20 can be coupled to a proximal portion of the core assembly 18 to provide an electrical current to the interventional element 100, as described in more detail below.

Figure 1B:
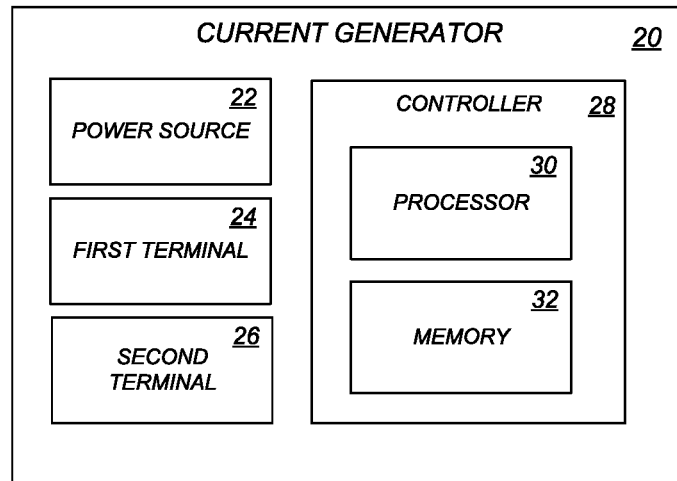
FIGS. 1B and 1C are schematic views of different embodiments of the current generator illustrated in FIG. 1A.
Figure 1C:
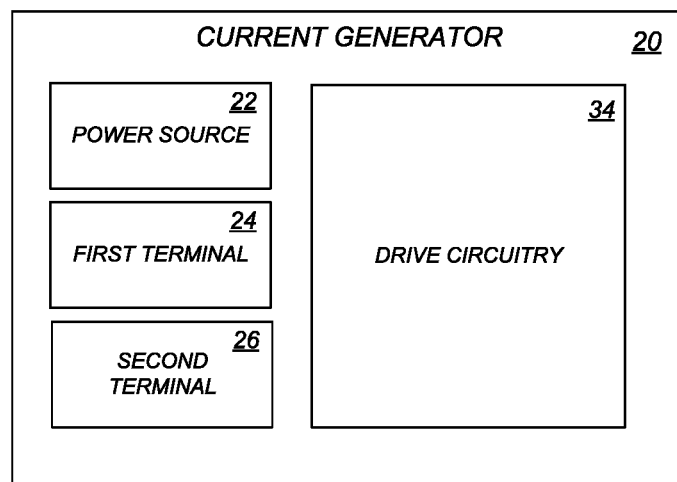

According to some embodiments, the current generator 20 can include an electrical generator configured to output medically useful electrical current. FIGS. 1B and 1C are schematic views of different embodiments of the current generator 20. With reference to FIG. 1B, the current generator 20 can include a power source 22, a first terminal 24, a second terminal 26, and a controller 28. The controller 28 includes a processor 30 coupled to a memory 32 that stores instructions (e.g., in the form of software, code or program instructions executable by the processor or controller) for causing the power source 22 to deliver electric current according to certain parameters provided by the software, code, etc. The power source 22 of the current generator 20 may include a direct current power supply, an alternating current power supply, or a power supply switchable between a direct current and an alternating current. The current generator 20 can include a suitable controller that can be used to control various parameters of the energy output by the power source or generator, such as intensity, amplitude, duration, frequency, duty cycle, and polarity. For example, the power supply 20 can provide a voltage of about 2 volts to about 28 volts and a current of about 0.5 mA to about 20 mA.

FIG. 1C illustrates another embodiment of the current generator 20, in which the controller 28 of FIG. 1B is replaced with drive circuitry 34. In this embodiment, the current generator 20 can include hardwired circuit elements to provide the desired waveform delivery rather than a software-based generator of FIG. 1B. The drive circuitry 34 can include, for example, analog circuit elements (e.g., resistors, diodes, switches, etc.) that are configured to cause the power source 22 to deliver electric current via the first and second terminals 24, 26 according to the desired parameters. For example, the drive circuitry 34 can be configured to cause the power source 22 to deliver periodic waveforms via the first and second terminals 24, 26.

Some systems for endovascular delivery of electrical current require the use of a return electrode (and/or associated return conductive path) that is wholly separated from the delivery electrode (and/or associated delivery conductive path). This may involve, for example, the use of a return electrode embedded within a catheter wall, or a needle puncturing the patient to complete a conductive pathway. In contrast, the present technology can provide, in one embodiment, an integrated core assembly that includes both a delivery electrode (and/or associated delivery conductive path) and a return electrode (and/or associated return conductive path) separated by an insulating material. According to one or more aspects of the present technology, electrically enhanced endovascular material removal can be facilitated by an electrode pair and associated delivery and return conductive paths provided within a treatment system, thereby avoiding the need to insert a needle into the patient to complete a circuit through the patient's tissue.

Figure 2A:
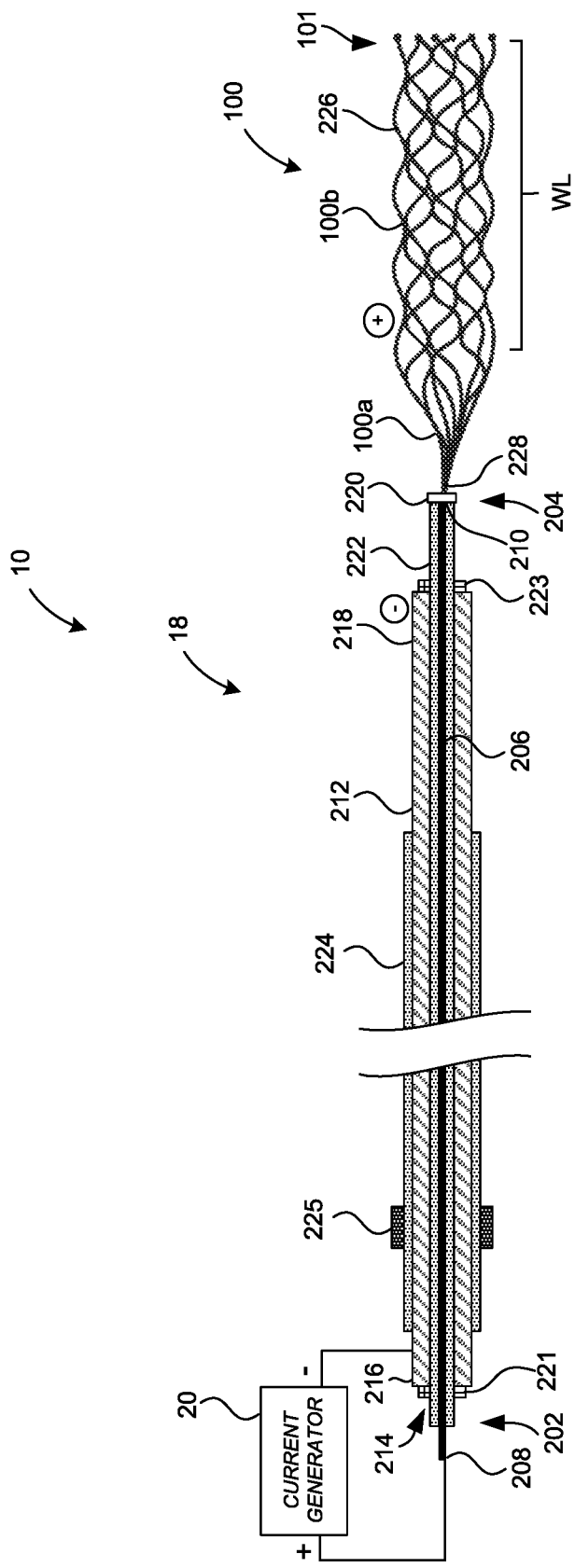
FIG. 2A is a side schematic cross-sectional view of the retrieval device shown in FIG. 1.

FIG. 2A is a side schematic cross-sectional view of the retrieval device shown in FIG. 1. The treatment system 10 includes the current generator 20, the core assembly 18, and the interventional element 100. As illustrated, the current generator 20 is electrically coupled to a proximal portion 202 of the core assembly 18, and the interventional element 100 is coupled to a distal portion 204 of the core assembly 18.

In some embodiments, the core assembly 18 can include multiple (e.g., two, or more than two) separate conductive paths or channels that provide electrical communication along the core assembly 18 with a corresponding number (e.g., two, or more than two) electrodes of the treatment system 10. The interventional element 100 can serve as one electrode (e.g., the delivery electrode) in electrical communication with one of the conductive paths of the core assembly 18. Another of the conductive paths of the core assembly 18 can be in electrical communication with another electrode (e.g., a return electrode) which can optionally form part of the core assembly 18. The various embodiments of the core assembly 18 can be sized for insertion into a bodily lumen, such as a blood vessel, and can be configured to push and pull a device such as the interventional element 100 along the bodily lumen.

In some embodiments, as seen for example in FIG. 2A, the core assembly 18 includes an elongate conductive shaft 206 and an elongate tubular member 212 having a lumen 214 through which the shaft 206 extends. The shaft 206 has a proximal portion 208 and a distal portion 210, and the tubular member 212 has a proximal portion 216 and a distal portion 218. Both the shaft 206 and the tubular member 212 are electrically conductive along their respective lengths. In some embodiments, the positions of the shaft 206 and the tubular member 212 are fixed relative to one another. For example, in some embodiments the shaft 206 is not slidable or rotatable with respect to the tubular member 212 such that the core assembly 18 can be pushed or pulled without relative movement between the shaft 206 and the tubular member 212 and/or other individual components of the core assembly 18.

In some embodiments, the shaft 206 can be a solid pushwire, for example a wire made of Nitinol or other metal or alloy. The shaft 206 may be thinner than would otherwise be required due to the additional structural column strength provided by the surrounding tubular member 212. The tubular member 212 can be a hollow wire, hypotube, braid, coil, or other suitable member(s), or a combination of wire(s), tube(s), braid(s), coil(s), etc. In some embodiments, the tubular member 212 can be a laser-cut hypotube having a spiral cut pattern along at least a portion of its length. The tubular member 212 can be made of stainless steel (e.g., 304

SS), Nitinol, and/or other alloy. In at least some embodiments, the tubular member 212 can have a laser cut pattern to achieve the desired mechanical characteristics (e.g., column strength, flexibility, kink-resistance, etc.).

Figure 2B:
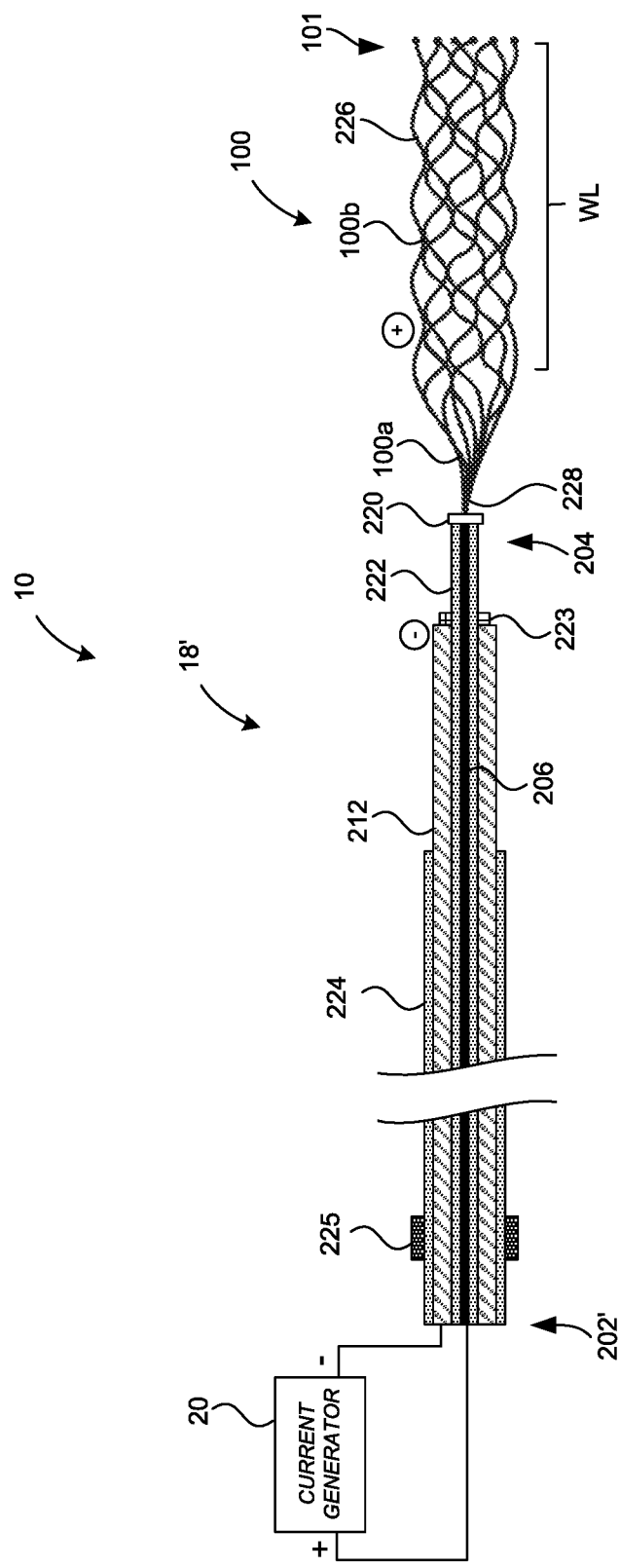
FIG. 2B is a side schematic cross-sectional view of another embodiment of a retrieval device.

The core assembly 18 can also include an adhesive or a mechanical coupler such as a crimped band or marker band 220 disposed at the distal end of the core assembly 18, and the marker band 220 can optionally couple the distal end of the core assembly 18 to the interventional element 100. The marker band 220 can be radiopaque, for example including platinum or other radiopaque material, thereby enabling visualization of the proximal end of the interventional element 100 under fluoroscopy. In some embodiments, additional radiopaque markers can be disposed at various locations along the treatment system 10, for example along the shaft 206, the tubular member 212, or the interventional element 100 (e.g., at the distal end of the interventional element 100). The core assembly 18 can further include a proximal restraint 221 and/or a distal restraint 223 that are configured to maintain the relative positions of the elongate tubular member 212 and the shaft 206. The proximal restraint 221 is positioned at or near the proximal end of the tubular member 212, and the distal restraint 223 can be positioned at or near the distal end of the tubular member 212. In some embodiments, the proximal and distal restraints 221, 223 comprise adhesive disposed radially around the shaft 206 such that the tubular member 208 cannot slide longitudinally with respect to the shaft 206. In other embodiments, the proximal and/or distal restraints 221, 223 can be crimped bands or other suitable structures that limit longitudinal movement of the tubular member 212 with respect to the shaft 206. In at least some embodiments, the proximal and/or distal restraints 221, 223 can be radiopaque. In at least some embodiments, the core assembly 18 also includes a first insulating layer or material 222 extending between the shaft 206 and the surrounding tubular member 212. The first insulating material 222 can be, for example, PTFE (polytetrafluoroethylene or TEFLON™) or any other suitable electrically insulating coating (e.g., polyimide, oxide, ETFE based coatings, or any suitable dielectric polymer). In some embodiments, the first insulating material 222 extends along substantially the entire length of the shaft 206. In some embodiments, the first insulating material 222 separates and electrically insulates the shaft 206 and the tubular member 212 along the entire length of the tubular member 212. In the embodiment illustrated in FIG. 2A, the first insulating material 222 does not cover the proximal-most portion of the shaft 206, providing an exposed region of the shaft 206 to which the current generator 20 can be electrically coupled. In some embodiments, for example as illustrated in FIG. 2B, the first insulating material 222 terminates proximally at the proximal terminus of the shaft 206, and the current generator 20 can electrically couple to the shaft 206 at its proximal terminus, for example using a coaxial connector.

The core assembly 18 can additionally include a second insulating layer or material 224 surrounding the tubular member 212 along at least a portion of its length. The second insulating layer 224 can be, for example, PTFE or any other suitable electrically insulative coating (e.g., polyimide, oxide, ETFE based coatings or any suitable dielectric polymer). In some embodiments, the distal portion 218 of the tubular member 212 is not covered by the second insulating layer 224, leaving an exposed conductive surface at the distal portion 218. In some embodiments, the length of the exposed distal portion 218 of the tubular member 212 can be at least (or equal to) 1, 2, 3, 4, 5, 6, or more inches. In some embodiments, the length of the exposed distal portion 218 of the tubular member 212 can be between at least 1 and 10 inches, or between 2 inches and 8 inches, or between 3 and 7 inches, or between 4 and 6 inches, or about 5 inches. This exposed portion of the distal portion 218 of the tubular member 212 provides a return path for current supplied to the delivery electrode (e.g. the entirety or a portion of the interventional element 100), as described in more detail below. In the embodiment illustrated in FIG. 2A, the second insulating material 224 does not cover the proximal-most portion of the tubular member 212, providing an exposed region of the tubular member 212 to which the current generator 20 can be electrically coupled. In some embodiments, for example as illustrated in FIG. 2B, the second insulating material 224 proximally terminates at the proximal end of the proximal terminus of the tubular member 212, and the current generator 20 can electrically couple to the tubular member 212 at its proximal terminus, for example using a coaxial connector.

The core assembly 18 can also include a retraction marker 225 in the proximal portion 216 of the tubular member 212. The retraction marker 225 can be a visible indicator to guide a clinician when proximally retracting an overlying catheter with respect to the core assembly 18. For example, the retraction marker 225 can be positioned such that when a proximal end of the overlying catheter is retracted to be positioned at or near the retraction marker 225, the distal portion 218 of the tubular member 212 is positioned distally beyond a distal end of the catheter. In this position, the exposed distal portion 218 of the tubular member 212 is exposed to the surrounding environment (e.g., blood, tissue, etc.), and can serve as a return electrode for the core assembly 18.

The proximal end 208 of the shaft 206 can be electrically coupled to the positive terminal of the current generator 20, and the proximal end of the tubular member 212 can be electrically coupled to the negative terminal of the current generator 20. During operation, the treatment system 10 provides an electrical circuit in which current flows from the positive terminal of the current generator 20, distally through the shaft 206, the interventional element 100, and the surrounding media (e.g., blood, tissue, thrombus, etc.) before returning back to the exposed distal portion 218 of the tubular member, proximally through the tubular member 212, and back to the negative terminal of the current generator 20.

As noted above, the current generator 20 can include a power source and either a processor coupled to a memory that stores instructions for causing the power source to deliver electric current according to certain parameters, or hardwired circuit elements configured to deliver electric current according to the desired parameters. The current generator 20 may be integrated into the core assembly 18 or may be removably coupled to the core assembly 18, for example via clips, wires, plugs or other suitable connectors. Particular parameters of the energy provided by the current generator 20 are described in more detail below with respect to FIGS. 4A-4D.

In certain embodiments, the polarities of the current generator 20 can be switched, so that the negative terminal is electrically coupled to the shaft 206 and the positive terminal is electrically coupled to the tubular member 212. This can be advantageous when, for example, attempting to attract predominantly positively charged material to the interventional element 100, or when attempting to break up a clot rather than grasp it with an interventional element. In some embodiments alternating current (AC) signals may be used rather than DC. In certain instances, AC signals may advantageously help break apart a thrombus or other material.

In the illustrated embodiments of FIGS. 2A-2B, the interventional element 100 can be a thrombectomy device having a low-profile configuration (not shown) when constrained within a delivery catheter (e.g., a microcatheter) and an expanded configuration for securing and/or engaging clot material or other obstructions within a blood vessel lumen (e.g., a cerebral blood vessel lumen) and/or for restoring blood flow within the blood vessel. The interventional element 100 has a proximal portion 100a coupled to the shaft 206 and a distal portion 100b. The interventional element 100 further includes an open cell framework or body 226 and a coupling region 228 extending proximally from the body 226. In some embodiments, a distal portion 100b of the interventional element 100 can be generally tubular (e.g., cylindrical), and the proximal portion 100a of the interventional element 100 can taper proximally to the coupling region 228. In various embodiments, the interventional element 100 can take any number of forms, for example a removal device, a thrombectomy device, a stent retriever, a stent, or other suitable medical device. For example, in some embodiments the interventional element 100 is a mesh structure formed of a superelastic material (e.g., Nitinol) or other resilient or self-expanding material configured to self-expand when released from the delivery catheter. The interventional element can be a metallic or electrically conductive thrombectomy device having a number of struts and open spaces between the struts, and the struts and spaces can be situated along the longitudinal direction of the interventional element, the radial direction, or both. For example, in some embodiments the interventional element 100 may be a stent and/or stent retriever, such as Medtronic's Solitaire™ Revascularization Device, Stryker Neurovascular's Trevo® ProVue™ Stentriever, or other suitable devices. In other embodiments, the interventional element 100 may include a plurality of braided filaments. Examples of suitable interventional elements 100 include any of those disclosed in U.S. Pat. No. 7,300,458, filed Nov. 5, 2007, U.S. Pat. No. 8,940,003, filed Nov. 22, 2010, U.S. Pat. No. 9,039,749, filed Oct. 1, 2010, and U.S. Pat. No. 8,066,757, filed Dec. 28, 2010, each of which is incorporated by reference herein in its entirety.

The interventional element 100 can be characterized by a working length WL, which can correspond to the region of the interventional element 100 configured to engage a thrombus or other material to be removed from a vessel lumen. In some embodiments, the non-working length portion of the interventional element 100 (i.e., proximal portion 100a) can be coated with a non-conductive material (e.g., PTFE or other suitable non-conductive coating) such that the coated region is not in electrical contact with the surrounding media (e.g., blood). As a result, the current carried by the shaft 206 to the interventional element 100 is only exposed to the surrounding media in the working length WL portion of the interventional element 100. This can advantageously concentrate the electrically enhanced attachment effect along the working length WL of the interventional element 100, where it is most useful, and thereby combine both the mechanical interlocking provided by the working length WL/body 226 and the electrical enhancement provided by the delivered electrical signal. In some embodiments, a distal region of the interventional element 100 may likewise be coated with a non-conductive material (e.g., PTFE or other suitable non-conductive coating), leaving only a central portion of the interventional element 100 having an exposed conductive surface. In some embodiments, some or all of the interventional element 100 can be coated with a conductive material, for example gold or other suitable conductor.

Figure 3A:
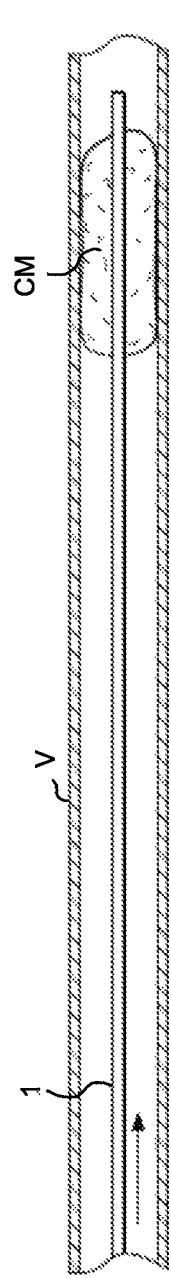
FIGS. 3A-3D illustrate a method of removing clot material from a blood vessel lumen using the retrieval device shown in FIGS. 1A and 2A.
Figure 3B:
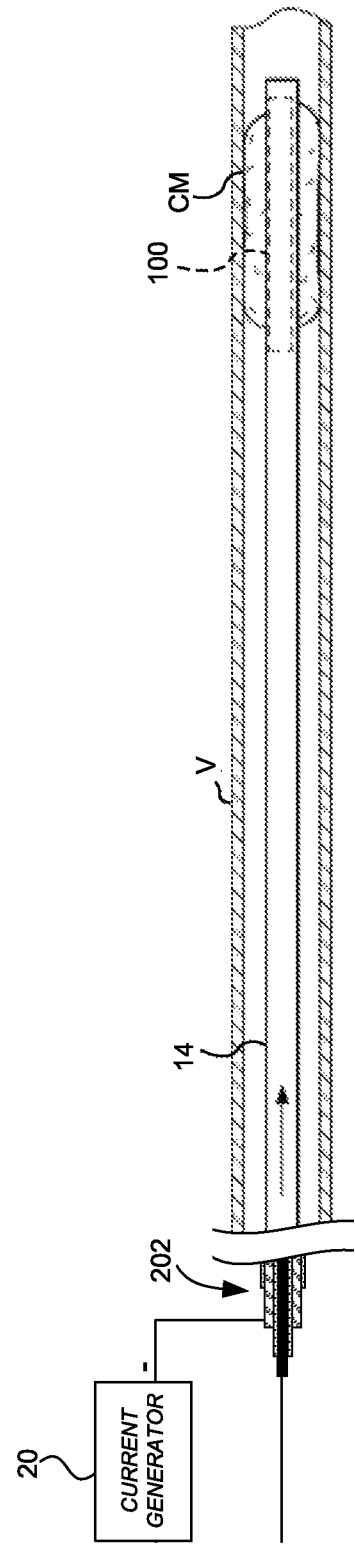
Figure 3C:
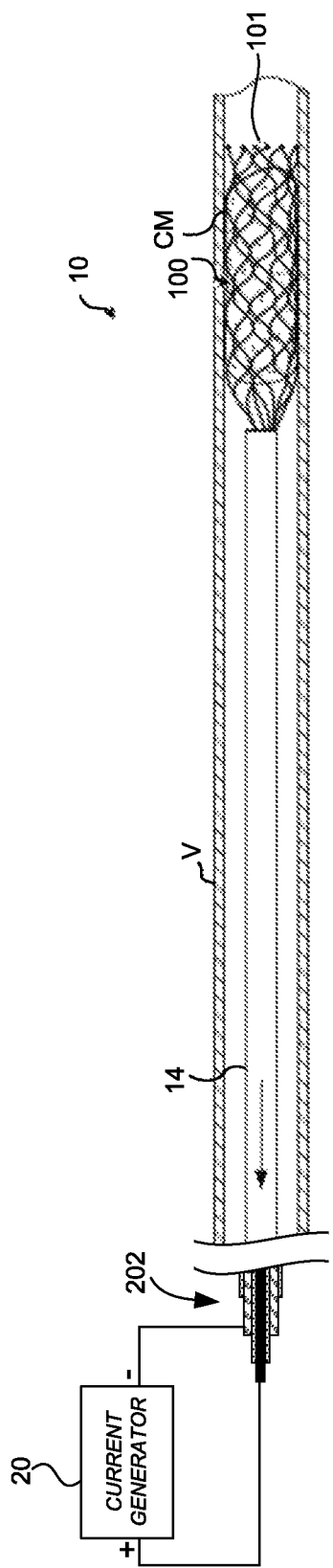

FIGS. 3A-3D illustrate a method of removing clot material from the lumen of a blood vessel V using the system 10 of the present technology. As shown in FIG. 3A, a guidewire 1 may be advanced through the clot material CM such that a distal terminus of the guidewire 1 is distal of the clot material CM. Next, a delivery catheter 14 may be delivered over the guidewire 1 so that a distal portion of the delivery catheter 14 is positioned at or near the clot material CM. As shown in FIG. 3B, in some embodiments the delivery catheter 14 may be advanced over the guidewire 1 through the clot material CM such that a distal terminus of the delivery catheter 14 is distal of the clot material CM. With the delivery catheter 14 in position, the guidewire 1 may be withdrawn. The interventional element 100 may then be advanced through the delivery catheter 14 in a low-profile configuration until a distal terminus 101 of the interventional element 100 (shown schematically in FIG. 3B) is at or adjacent the distal terminus of the delivery catheter 14. As shown in FIG. 3C, the delivery catheter 14 may then be withdrawn proximally relative to the interventional element 100 to release the interventional element 100, thereby allowing the interventional element 100 to self-expand within the clot material CM. As the interventional element 100 expands, the interventional element 100 engages and/or secures the surrounding clot material CM, and in some embodiments may restore or improve blood flow through the clot material CM. In some embodiments, the interventional element 100 may be expanded distal of the clot material CM such that no portion of the interventional element 100 is engaging the clot material CM while the interventional element 100 is in the process of expanding toward the vessel wall. In some embodiments, the interventional element 100 is configured to expand into contact with the blood vessel wall, or the interventional element 100 may expand to a diameter that is less than that of the blood vessel lumen such that the interventional element 100 does not engage the entire circumference of the blood vessel wall.

Once the interventional element 100 has been expanded into the clot material CM, the interventional element 100 can grip the clot material CM, by virtue of its ability to mechanically interlock with the clot material CM as well as its ability to electrically attract, adhere, and/or attach to the clot material CM as a result of the delivery of electrical current to the interventional element 100. The current generator 20, which is electrically coupled to the proximal end 202 of the core assembly 18, can deliver an electrical signal to the interventional element 100 before or after the interventional element 100 has been released from the catheter 14 into the anatomical vessel V (e.g., an intracranial vessel) and/or expanded into the clot material CM. The interventional element 100 can be left in place or manipulated within the vessel V for a desired time period while the electrical signal is being delivered. Positive current delivered to the interventional element 100 can attract negatively charged constituents of the clot material CM, thereby enhancing the grip of the interventional element 100 on the clot material CM. This allows the interventional element 100 to be used to retrieve the clot material CM with reduced risk of losing grip on the thrombus or a piece thereof, which can migrate downstream and cause additional vessel blockages in areas of the brain that are more difficult to reach.

Figure 3D:
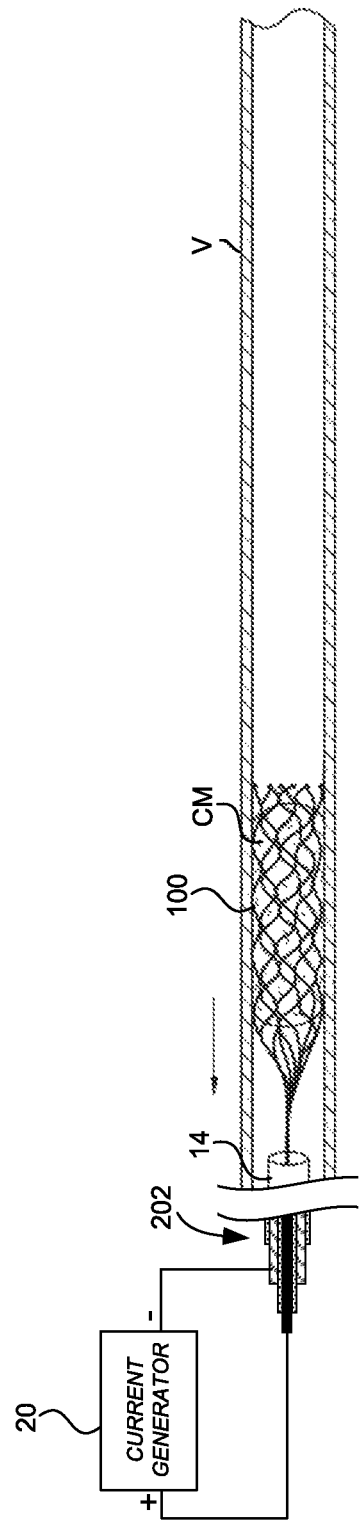

With reference to FIG. 3D, once the interventional element 100 has engaged and captured the clot material CM, the clot material CM can be removed. For example, the interventional element 100 with the clot material CM gripped thereby, can be retracted (for example, along with the catheter 14) proximally. The catheter 14, interventional element 100, and associated clot material CM may then be withdrawn from the patient, optionally through one or more larger surrounding catheters. During this retraction, the interventional element 100 can grip the clot material CM electrically and/or electrostatically, e.g., via the application of current from a current generator as discussed herein. (As used herein with reference to gripping or retrieving thrombus or other vascular/luminal material, or to apparatus for this purpose, "electrical" and its derivatives will be understood to include "electrostatic" and its derivatives.) Accordingly, the interventional element 100 can maintain an enhanced or electrically and/or electrostatically enhanced grip on the clot material CM during retraction. In other embodiments, the current generator 20 may cease delivery of electrical signals to the interventional element 100 prior to retraction of the interventional element 100 with respect to the vessel V. In some embodiments, the interventional element 100 and clot material CM form a removable, integrated thrombus-device mass wherein the connection of the thrombus to the device is electrically enhanced, e.g. via the application of current as discussed herein.

Selected Embodiments of Waveforms for Electrically Enhanced Retrieval

FIGS. 4A-4D show various electrical waveforms for use with the retrieval devices of the present technology. Although the waveforms and other power delivery parameters disclosed herein can be used with the devices and methods described above with respect to FIGS. 1A-3D, the waveforms and other parameters are also applicable to other device configurations and techniques. For example, the return electrode can be provided along the catheter wall, as a separate conductive member extending within the catheter lumen, as a needle electrode provided elsewhere in the body, etc. In each of these device configurations, the power delivery parameters and waveforms can be beneficially employed to promote clot adhesion without damaging surrounding tissue. Additionally, although the waveforms and other power delivery parameters disclosed herein may be used for treating a cerebral or intracranial embolism, other applications and other embodiments in addition to those described herein are within the scope of the technology. For example, the waveforms and power delivery parameters disclosed herein may be used to electrically enhance removal of emboli from body lumens other than blood vessels (e.g., the digestive tract, etc.) and/or may be used to electrically enhance removal of emboli from blood vessels outside of the brain (e.g., pulmonary blood vessels, blood vessels within the legs, etc.).

While applying a continuous uniform direct current (DC) electrical signal to negatively charge the interventional element can improve its attachment to the thrombus, this can risk damage to surrounding tissue (e.g., ablation), and sustained current at a relatively high level may also be thrombogenic (i.e., may generate new clots). For achieving effective clot-grabbing without ablating tissue or generating substantial new clots at the target site, periodic waveforms have been found to be particularly useful. Without wishing to be bound by theory, the clot-adhesion effect appears to be most closely related to the peak current of the delivered electrical signal. Periodic waveforms can advantageously provide the desired peak current without delivering excessive total energy or total electrical charge. Periodic, non-square waveforms in particular are well suited to deliver a desired peak current while reducing the amount of overall delivered energy or charge as compared to either uniform applied current or square waveforms.

Figure 4A:
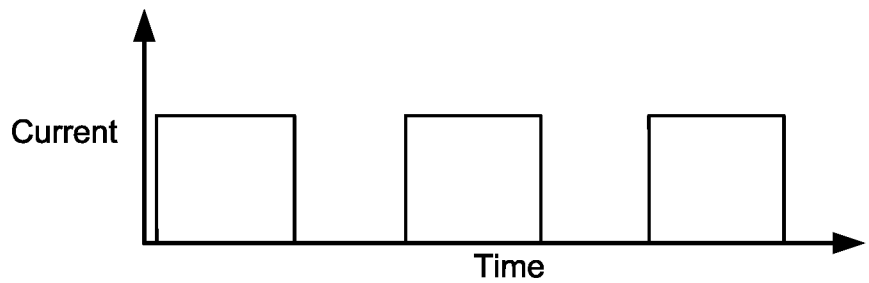
FIGS. 4A-4D illustrate sample waveforms for electrically enhanced removal of material from vessel lumens in accordance with one or more embodiments of the present disclosure.
Figure 4B:
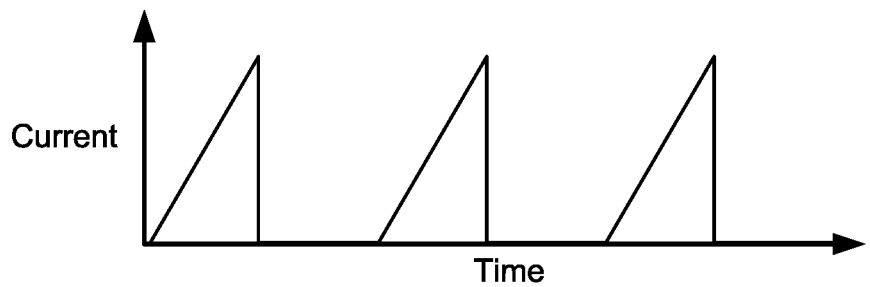
Figure 4C:
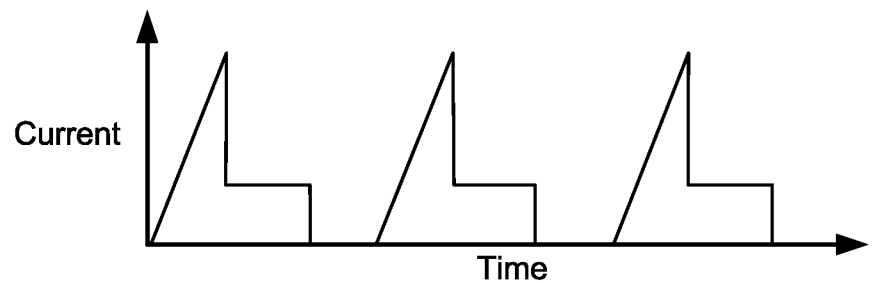
Figure 4D:
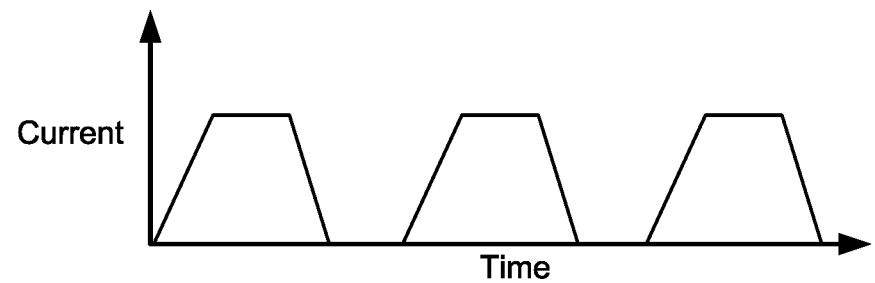

FIGS. 4A-4D illustrate various periodic waveforms that can be used with the devices and methods described above with respect to FIGS. 1A-3D, as well as with other devices and techniques. Electrical power can be delivered according to these waveforms as pulsed direct current. FIGS. 4A and 4B illustrate periodic square and triangular waveforms, respectively. These two waveforms have the same amplitude, but the triangular waveform is able to deliver the same peak current as the square waveform, with only half of the total charge delivered, and less total energy delivered. FIG. 4C illustrates another pulsed-DC or periodic waveform which is a composite of a square waveform and a triangular waveform. This superposition of a triangular waveform and a square waveform shown in FIG. 4C delivers additional efficacy compared to the triangular waveform of FIG. 4B while nonetheless delivering less overall energy than the square waveform of FIG. 4A. This is because the delivered energy is proportional to the square of current and the brief high peak in the composite waveform of FIG. 4C ensures that current is supplied without dispensing excessive energy. FIG. 4D illustrates yet another non-square waveform, in this case a trapezoidal waveform in which "ramp-up" and "ramp-down" portions at the beginning and end of each pulse provide periods of reduced current compared to square waveforms. In other embodiments, different non-square waveforms can be used, including a superposition of a square waveform with any non-square waveform, depending on the desired power delivery characteristics.

The waveform shape (e.g., pulse width, duty cycle, amplitude) and length of time can each be selected to achieve desired power delivery parameters, such as overall electrical charge, total energy, and peak current delivered to the interventional element. In some embodiments, the overall electrical charge delivered to the interventional element can be between about 30-1200 mC, or between about 120-600 mC. According to some embodiments, the total electrical charge delivered to the interventional element may be less than 600 mC, less than 500 mC, less than 400 mC, less than 300 mC, less than 200 mC, or less than 100 mC.

In some embodiments, the total energy delivered to the interventional element can be between about 0.75-24,000 mJ, or between about 120-24,000 mJ, or between about 120-5000 mJ. According to some embodiments, the total energy delivered to the interventional element may be less than 24,000 mJ, less than 20,000 mJ, less than 15,000 mJ, less than 10,000 mJ, less than 5,000 mJ, less than 4,000 mJ, less than 3,000 mJ, less than 2000 mJ, less than 1,000 mJ, less than 900 mJ, less than 800 mJ, less than 700 mJ, less than 600 mJ, less than 500 mJ, less than 400 mJ, less than 300 mJ, or less than 200 mJ, or less than 120 mJ, or less than 60 mJ, or less than 48 mJ, or less than 30 mJ, or less than 12 mJ, or less than 6 mJ, or less than 1.5 mJ.

In some embodiments, the peak current delivered can be between about 0.5-20 mA, or between about 0.5-5 mA. According to some embodiments, the peak current delivered may be greater than 0.5 mA, greater than 1 mA, greater than 1.5 mA, greater than 2 mA, greater than 2.5 mA, or greater than 3 mA.

The duration of power delivery is another important parameter that can be controlled to achieve the desired clot-adhesion effects without damaging tissue at the target site or generating new clots. In at least some embodiments, the total energy delivery time can be no more than 1 minute, no more than 2 minutes, no more than 3 minutes, no more than 4 minutes, or no more than 5 minutes. According to some embodiments, the total energy delivery time may be less about 30 seconds, less than about 1 minute, less than about 90 seconds, or less than about 2 minutes. As used herein, the "total energy delivery time" refers to the time period during which the waveform is supplied to the interventional element (including those periods of time between pulses of current).

The duty cycle of the applied electrical signal can also be selected to achieve the desired clot-adhesion characteristics without ablating tissue or promoting new clot formation. In some embodiments, the duty cycle can be between about 5% about 99% or between about 5% to about 20%. According to some embodiments, the duty cycle may be about 10%, about 20%, about 30%, about 40%, or about 50%. In yet other embodiments, a constant current may be used, in which the duty cycle is 100%. For 100% duty cycle embodiments, a lower time or current may be used to avoid delivering excess total energy to the target site.

Table 1 presents a range of values for power delivery parameters of different waveforms. For each of the conditions set forth in Table 1, a resistance of 1 kohm and a frequency of 1 kHz (for the Square, Triangle, and Composite conditions) was used. The Constant conditions represent a continuous and steady current applied for the duration, i.e. 100% duty cycle. The Peak Current 1 column represents the peak current for the corresponding waveform. For the Composite conditions, the Peak Current 2 column indicates the peak current of the second portion of the waveform. For example, referring back to FIG. 4C, Peak Current 1 would correspond to the current at the top of the triangular portion of the waveform, while Peak Current 2 would correspond to the current at the top of the square portion of the waveform.

improved clot adhesion while reducing the risk of damaging tissue at the target site or promoting new clot formation. Table 1 also indicates that the Triangle and Composite conditions achieve higher peak currents with lower overall charge delivered than the corresponding Square conditions. For example, condition Square 3 has a peak current of 20 mA and a total charge delivered of 240 mC, while condition Triangle 2 has a peak current of 20 mA but a total charge delivered of only 120 mC, and condition Composite 1 has a peak current of 20 mA and a total charge delivered of only 144 mC. As such, these non-square waveforms provide additional benefits by delivering desirable peak current while reducing the overall charge delivered to the target site.

Although Table 1 represents a series of waveforms with a single frequency (1 kHz), in some embodiments the frequency of the pulsed-DC waveforms can be controlled to achieve the desired effects. For example, in some embodiments the frequency of the waveform can be between 1 Hz and 1 MHz, between 1 Hz and 1 kHz, or between 500 Hz to 1 kHz.

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented

TABLE 1

| Condition | Peak Current 1 (mA) | Peak Current 2 (mA) | Duty Cycle 1 (%) | Duty Cycle 2 (%) | Peak Voltage (V) | Pulse Width (ms) | Total Time (s) | Total Charge (mC) | Total Energy (@ R = 1000 ohm) (mJ) | Total Energy (@ R = 50 ohm) (mJ) |
|---|---|---|---|---|---|---|---|---|---|---|
| Constant 1 | 2 | 0 | 100 | 0 | 2 | n/a | 120 | 240 | 480 | 24 |
| Constant 2 | 2 | 0 | 100 | 0 | 2 | n/a | 60 | 120 | 240 | 12 |
| Constant 3 | 10 | 0 | 100 | 0 | 10 | n/a | 60 | 600 | 6000 | 300 |
| Constant 4 | 20 | 0 | 100 | 0 | 20 | n/a | 60 | 1200 | 24000 | 1200 |
| Constant 5 | 10 | 0 | 100 | 0 | 10 | n/a | 120 | 1200 | 12000 | 600 |
| Constant 6 | 1 | 0 | 100 | 0 | 1 | n/a | 120 | 120 | 120 | 6 |
| Constant 7 | 0.5 | 0 | 100 | 0 | 1 | n/a | 120 | 60 | 30 | 1.5 |
| Constant 8 | 0.5 | 0 | 100 | 0 | 1 | n/a | 60 | 30 | 15 | 0.75 |
| Square 1 | 10 | 0 | 10 | 0 | 10 | 0.1 | 120 | 120 | 1200 | 60 |
| Square 2 | 4 | 0 | 50 | 0 | 4 | 0.5 | 120 | 240 | 960 | 48 |
| Square 3 | 20 | 0 | 10 | 0 | 20 | 0.1 | 120 | 240 | 4800 | 240 |
| Square 4 | 20 | 0 | 10 | 0 | 20 | 0.1 | 60 | 120 | 2400 | 120 |
| Square 5 | 10 | 0 | 10 | 0 | 10 | 0.1 | 60 | 60 | 600 | 30 |
| Triangle 1 | 10 | 0 | 10 | 0 | 10 | 0.1 | 120 | 60 | 1200 | 60 |
| Triangle 2 | 20 | 0 | 10 | 0 | 20 | 0.1 | 120 | 120 | 4800 | 240 |
| Composite 1 | 20 | 1 | 10 | 20 | 20 | 0.3 | 120 | 144 | 4824 | 264 |
| Composite 2 | 10 | 2 | 10 | 20 | 10 | 0.3 | 120 | 108 | 1296 | 156 |

As seen in Table 1, the periodic waveforms (Square, Triangle, and Composite conditions) achieve higher peak currents with lower overall charge delivered than the corresponding Constant conditions. For example, in condition Constant 4, a peak current of 20 mA corresponds to a total energy delivered of 24,000 mJ, while condition Square 3 delivers a peak current of 20 mA with a total energy of only 4,800 mJ. Conditions Triangle 2 and Composite 1 similarly deliver lower total energy while maintaining a peak current of 20 mA. Since clot-adhesion appears to be driven by peak current, these periodic waveforms can therefore offer herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

We claim:

1. A medical device comprising:
   a core assembly having a distal portion configured to be intravascularly positioned at a treatment site within a blood vessel lumen, the core assembly comprising:
   a hypotube operably coupled to a first electrical terminal, the hypotube having a spiral cut pattern along its length, a proximal portion, a distal portion, and a lumen extending therethrough;
   a pushwire operably coupled to a second electrical terminal, the pushwire extending through the hypotube lumen; and
   an insulating layer disposed between the hypotube and the pushwire, the insulating layer extending from the proximal portion of the hypotube to the distal portion of the hypotube; and
   an interventional element coupled to a distal end of the pushwire.

2. The medical device of claim 1, wherein the interventional element comprises a thrombectomy device.

3. The medical device of claim 1, wherein the interventional element comprises a stent retriever.

4. The medical device of claim 1, wherein the interventional element comprises a removal device.

5. The medical device of claim 1, wherein the interventional element comprises a catheter.

6. The medical device of claim 1, wherein the interventional element is in electrical communication with the pushwire.

7. The medical device of claim 1, wherein the first electrical terminal is negative and the second electrical terminal is positive.

8. The medical device of claim 1, further comprising a second insulating layer disposed around an outer surface of a proximal portion of the hypotube.

9. The medical device of claim 8, wherein the outer surface of a distal portion of the hypotube is uncovered by the second insulating layer.

10. The medical device of claim 1, wherein the insulating layer comprises PTFE, polyimide, ETFE, or a dielectric polymer.

11. The medical device of claim 1, wherein the pushwire is fixed with respect to the hypotube.

12. The medical device of claim 1, further comprising a radiopaque marker disposed at a distal end of the pushwire.

13. The medical device of claim 1, wherein, when the interventional element is in the presence of an electrolytic medium and voltage is supplied to the first and second electrical terminals, current flows from the interventional element to the hypotube.

14. The medical device of claim 1, wherein a portion of the interventional element is coated with a non-conductive material.

15. A medical device delivery system, comprising:
   a medical device coupled to a distal end of an elongate shaft, the shaft configured to be electrically coupled to a first terminal;
   a hypotube surrounding at least a portion of the shaft, the hypotube having a spiral cut pattern along its length and configured to be electrically coupled to a second terminal;
   a first insulating material separating the shaft and the hypotube; and
   a second insulating material surrounding at least a portion of the hypotube.

16. The medical device delivery system of claim 15, wherein the positions of the shaft and the hypotube are fixed relative to one another.

17. The medical device delivery system of claim 15, wherein the hypotube is not slidable with respect to the shaft.

18. The medical device delivery system of claim 15, wherein the medical device comprises a thrombectomy device.

19. The medical device delivery system of claim 15, wherein the medical device comprises a stent retriever.

20. The medical device delivery system of claim 15, wherein the medical device comprises a removal device.

21. The medical device delivery system of claim 15, wherein the medical device is in electrical communication with the shaft.

22. The medical device delivery system of claim 15, wherein the first electrical terminal is positive and the second electrical terminal is negative.

23. The medical device delivery system of claim 15, wherein an outer surface of a distal portion of the hypotube is uncovered by the second insulating material.

24. The medical device delivery system of claim 15, wherein the first insulating material and the second insulating material each comprises PTFE, polyimide, ETFE, or a dielectric polymer.

25. The medical device delivery system of claim 15, further comprising a radiopaque marker disposed at a distal end of the shaft.

26. The medical device delivery system of claim 15, wherein, when the medical device is in the presence of an electrolytic medium and voltage is supplied to the first and second electrical terminals, current flows from the medical device to the hypotube.

27. The medical device delivery system of claim 15, wherein a portion of the medical device is coated with a non-conductive material.

28. The medical device delivery system of claim 1, wherein the hypotube has a spiral cut pattern along at least a portion of its length.

* * * * *

UNITED STATES PATENT AND TRADEMARK OFFICE
CERTIFICATE OF CORRECTION

PATENT NO. : 11,058,444 B2  
APPLICATION NO. : 15/838214  
DATED : July 13, 2021  
INVENTOR(S) : Gaurav Girdhar et al.

Page 1 of 1

It is certified that error appears in the above-identified patent and that said Letters Patent is hereby corrected as shown below:

On the Title Page

Item [72]  
Line 3, delete "Andy," and insert -- Andyanhdzung, --, therefor.

Signed and Sealed this  
Twenty-seventh Day of August, 2024

Katherine Kelly Vidal  
*Director of the United States Patent and Trademark Office*